(12) United States Patent
Skuse et al.

(10) Patent No.: US 7,999,219 B2
(45) Date of Patent: Aug. 16, 2011

(54) RADIOGRAPHIC CALIBRATION

(75) Inventors: Kevin F. Skuse, Bristol (GB); Scott Kennerell, Nottingham (GB)

(73) Assignee: Rolls-Royce PLC, London (GB)

( * ) Notice: Subject to any disclaimer, the term of this patent is extended or adjusted under 35 U.S.C. 154(b) by 323 days.

(21) Appl. No.: 12/226,912

(22) PCT Filed: May 3, 2007

(86) PCT No.: PCT/GB2007/001629
§ 371 (c)(1),
(2), (4) Date: Oct. 31, 2008

(87) PCT Pub. No.: WO2007/141469
PCT Pub. Date: Dec. 13, 2007

(65) Prior Publication Data
US 2009/0161833 A1    Jun. 25, 2009

(30) Foreign Application Priority Data

Jun. 2, 2006 (GB) .................................. 0610885.6

(51) Int. Cl.
*G01D 18/00* (2006.01)
(52) U.S. Cl. .................................. 250/252.1; 378/207
(58) Field of Classification Search ............... 250/505.1, 250/252.1; 378/162, 163, 207
See application file for complete search history.

(56) References Cited

U.S. PATENT DOCUMENTS

| 4,408,124 A | 10/1983 | Paras |
| 4,460,832 A | 7/1984 | Bigham |
| 4,625,168 A | 11/1986 | Meyer et al. |
| 5,056,130 A * | 10/1991 | Engel ............................ 378/207 |
| 5,416,816 A | 5/1995 | Wenstrup et al. |
| 6,658,089 B1 | 12/2003 | Mohr et al. |

FOREIGN PATENT DOCUMENTS

JP    A-09-164131    6/1997

OTHER PUBLICATIONS

Peer et al., "Resolution requirements for monitor viewing of digital flat-panel detector radiographs: a contrast detail analysis," *European Radiology*, 2003, vol. 13, No. 2, pp. 413-417.
Hanson et al., "Computed tomography using proton energy loss," *Physics in Medicine and Biology*, 1981, vol. 26, No. 6, pp. 965-983.
Sawant et al., "Segmented crystalline scintillators: Empirical and theoretical investigation of a high quantum efficiency EPID based on an initial engineering prototype CsI(TI) detector," *Medical Physics*, 2006, vol. 33, No. 4, pp. 1053-1066.

* cited by examiner

*Primary Examiner* — David Porta
*Assistant Examiner* — Faye Boosalis
(74) *Attorney, Agent, or Firm* — Oliff & Berridge, PLC

(57) ABSTRACT

By providing holes (32, 45, 46, 47, 51, 52, 53) in hole groups (31, 41, 42, 43) (generally in a triangular orientation for a range of incremental hole sizes) it is possible to provide an image quality indicator which provides a minimum defect size which can be determined based upon contrast sensitivity and spatial resolution. Each hole (32, 45, 46, 47, 51, 52, 53) has a diameter (d) which is the same as its depth (d) and the three holes (32, 45, 46, 47, 51, 52, 53) in a hole group (31, 41, 42, 43) have a spacing (s) the equivalent of the hole diameter (d) and depth (d). The value of the spacing (s), diameter (d) and depth (d) is defined as a calibration value and is generally a percentage of the material thickness.

9 Claims, 2 Drawing Sheets

RADIOGRAPHIC CALIBRATION

The present invention relates to radiographic calibration and more particularly to radiographic calibration with respect to contrast and spatial aspects with film or filmless systems using a digital camera or other sensor devices.

It is a requirement with regard to components, particularly in safety critical environments, to inspect those components for defects such as cracks. One technique with regard to such inspection is by utilising an interrogatory radiation such as x-rays which pass through the component with varying degrees of attenuation in order to create an image upon a film or other sensor arrangement. Typically, in the past this image has been formed upon a photographic plate with the necessary high level of resolution in order to detect defects such as cracking to a desired level of accuracy.

It will be understood that the accuracy of inspection is dependent upon a number of factors, including the material from which the component is formed, the capabilities of the inspection system such as a photographic plate, and the nature of the defect. In order to provide in situ referencing, typically a calibration gauge is provided for comparison. It will be understood that calibration with regard to both contrast sensitivity and spatial resolution are important. A number of techniques have been developed in order to provide this calibration based upon graduated incremental wire or hole or step calibration gauges in the form of a plate on which the wire or through which a hole passes or upon which graduated steps are formed of varying thickness to provide the necessary calibration reference.

It will be understood that radiation such as x-rays as indicated are attenuated. It is this attenuation which provides the absorption contrast identified by the detector, such as the photographic plate or a camera. If the radiation is absorbed then this will be identified by the camera whilst if the radiation is not absorbed then this will similarly be noticeable in an image created. Contrast simply relates to the ability to identify inconsistencies in the image generally in a plane, while spatial resolution relates to identifying depth related inconsistencies in the image. Thus, holes can be utilised as identifiable references for contrast sensitivity, whilst different wire thicknesses enable a determination as to the absorption depth of the interrogatory radiation to determine the minimum volumetric defect size that an inspection system can detect.

As indicated above, traditionally photographic plates have been utilised which, when subject to exposure, may be able to identify and provide resolution to the order of 4 microns defect size sensitivity both in terms of contrast and spatial resolution. However, such photographic plates require developing and therefore can be inconvenient for large scale inspection of a high number of components. In such circumstances, more recently filmless systems using a digital sensor or other sensory device have been used in order to create images. These digital surveys typically only have a resolution in the order of, at best, 50 microns. In such circumstances, with filmless detector systems it is generally necessary to provide a number of different image quality indicators (IQIs) with one image quality indicator used for contrast sensitivity and another image quality indicator used for spatial resolution. Contrast sensitivity is generally determined using accurately formed holes which pass through a gauge plate, whilst spatial resolution is typically determined using incrementally graded wires.

In accordance with the present invention, there is provided a gauge for providing calibration when exposed to interrogatory radiation in an imaging system, the gauge comprising holes characterised in that the holes are arranged in a hole group, the holes having a diameter, a depth and a spacing to other holes of the hole group of substantially the same calibration value, the diameter provides a reference for assessing contrast resolution, whilst the depth and spacing of the holes provides a reference dependent upon attenuation of an interrogatory radiation in the material of the gauge between the holes for assessing spatial resolution.

Preferably, there are three holes in the hole group arranged in a triangular pattern. Normally, there is a plurality of hole groups within the gauge. Generally, all the hole groups are integrally formed within an object for inspection.

Possibly, the gauge comprises a separate element to an object for inspection.

Typically, the calibration value relates to a percentage of a thickness of the gauge. Generally, where there is a plurality of hole groups, the calibration values are 2 percent, 4 percent, 6 percent and 8 percent of the thickness of the gauge. Possibly, the gauge has a thickness in the order of 2 mm.

Possibly, the gauge may be associated with shims in order to vary the thickness of the gauge.

Also in accordance with the present invention there is provided a gauge for a particular component, the gauge as described above.

Typically, the gauge is integrally formed with the particular component. Alternatively, the gauge is separable from the particular component.

Preferably, the gauge is made from the same material as the particular component. Alternatively, the gauge is made from a material having substantially the same radiological nature as the material from which the particular component is formed.

Preferably, the interrogatory radiation is one of the group comprising X-rays, gamma radiation and neutron radiation.

Embodiments of aspects of the present invention will now be described by way of example only with reference to the accompanying drawings in which.

Figure 1:
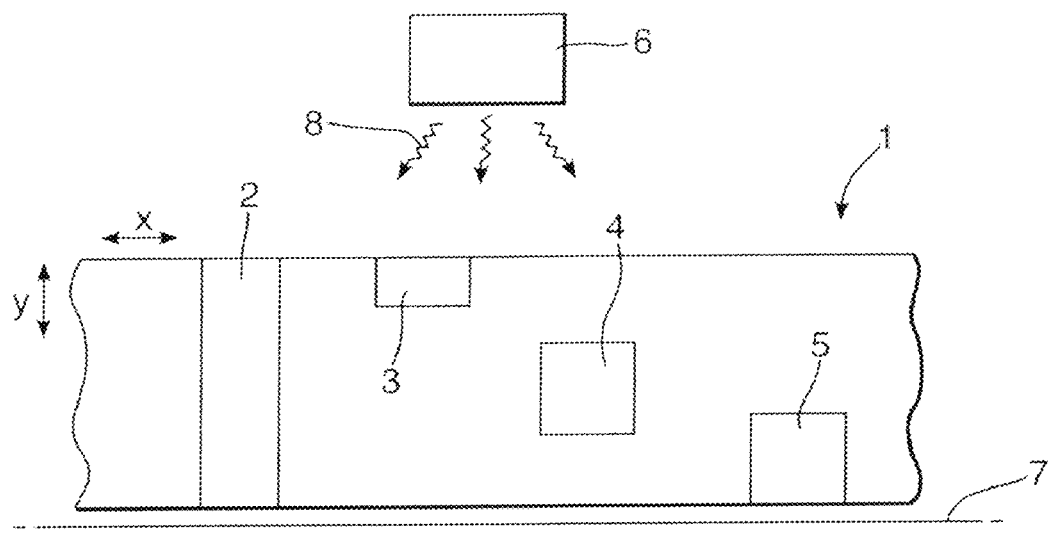
FIG. 1 is a schematic cross-section of a component subject to an interrogatory radiation such as x-rays.
Figure 2:
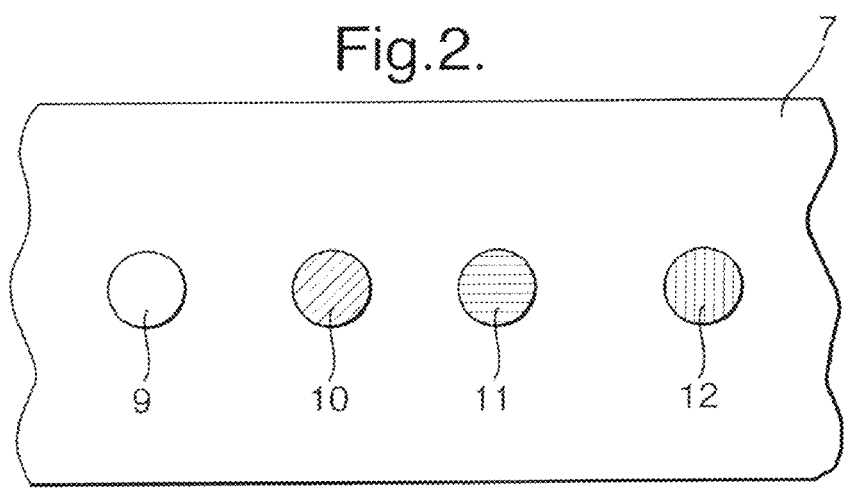
FIG. 2 is a plan view of the image responses for the different features depicted in FIG. 1.

FIG. 1 provides a schematic illustration of an object 1 such as a gauge or a component including a number of features 2, 3, 4, 5 which may relate to defects if in a component. A source of interrogatory radiation 6 is provided such that the object 1 is bathed in an interrogatory radiation 8 which is typically x-rays such that a detected image 7 is provided. Previously this image 7 was recorded on a photographic plate which had sufficient sensitivity to detect in the order of 4 microns in both contrast sensitivity and spatial resolution. With such a prior approach, the photographic plate would be able to quantify the features 2, 3, 4, 5 both in terms of contrast sensitivity in the direction of the plane of the component 1, that is to say in the direction of arrowheads X, as well as spacially, that is to say inwardly of the component in the direction of arrowhead Y to a resolution as indicated in the order of four microns. Filmless systems using digital image sensor devices are replacing photographic plates and have a low resolution which is in the order of fifty microns which is generally still acceptable but can lead to spurious results.

It will be understood that generally specifiers of component quality will determine a level of acceptability with regard to contrast sensitivity and also with regard to spatial resolution which may be different. For example, a 2 percent of component thickness contrast sensitivity may be specified whilst spatial resolution may be specified in the order of 0.125 mm or 0.25 mm for castings.

Filmless systems have a spatial resolution based upon pixel or voxel (volumetric pixel) size such that it is necessary to provide a separate measure of spatial resolution as well as contrast resolution.

As indicated above, previously contrast resolution and spatial resolution were determined separately but neither of these techniques provide reference as to the actual minimum detectable defect size. Aspects of the present invention provide a calibration gauge which gives the smallest detectable defect size based upon the material type and thickness and material volume removed or missing as a result of a defect.

As indicated, FIG. 1 illustrates an object 1 incorporating a number of features, 2, 3, 4, 5. Feature 2 relates to a hole which passes completely through the object 1 such that radiation from the source 6 passes through the object 1 without attenuation to create an image 9 whose dimensions are dependent upon the contrast sensitivity of the system. Features 3, 4, 5 relate to defects within the object 1 which do not extend completely through the object 1 but nevertheless change the volume of material through which the radiation 8 passes before forming an image 7. In such circumstances, images 10, 11, 12 are as a result of the radiation passing through the object 1. In such circumstances, the images 10, 11, 12 will generally be blurred or of less intensity than the image 9 but nevertheless may be detectable elements within the image 7. It will be noted that the defects or features 3, 4, 5 relate respectively to a defect in an upper surface of the object 1, internally within the object 1 and on the bottom surface of the object 1.

A more desirable calibration gauge would be able to simultaneously provide an indication as to the contrast sensitivity of the system as well as the spatial resolution of the system which will be dependent upon being able to identify the reduced intensity of the images 10, 11, 12 as a result of radiation absorption.

It will also be understood that it is important to be able to differentiate between defects in a component which are within a determinable distance of each other as well as whether there is one defect or two defects. Again, a more appropriate calibration gauge would be able to provide that function. It will be understood that the purpose of a calibration gauge is to provide a reference image quality indicator with respect to reliability of determining defects within an object such as a component to be inspected.

An alternate name for a calibration gauge is an image quality indicator which will more appropriately express the reference nature with respect to the reliability of determining defects. However, image quality indicators do not provide an infallible guarantee of detecting defects equivalent in size to the contrast sensitivity value obtained. It will be understood that defects as indicated above can be across as well as through the depth of an object with regard to the orientation of the source, object and detector, whether that be film or a camera or other sensor. Thus, the radiation absorption quotient of the material has an effect.

Figure 3:
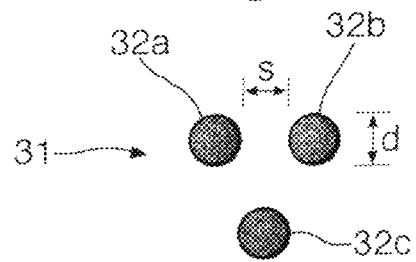
FIG. 3 is a schematic illustration of a hole group for a calibration gauge in accordance with aspects of the present invention.

Aspects of the present invention provide a calibration gauge which can provide an image quality indicator for both contrast sensitivity and spatial resolution. The gauge is typically made from the same material as the material under inspection or will be made from a material having a density that is radiographically similar. The gauge may be a separate plate located upon or adjacent the object to be inspected or the gauge may be formed in a surface of the object. Generally, the calibration gauge consists of a series of holes arranged as depicted in FIG. 3. Aspects of the present invention are described with regard to a hole group comprising three holes but it will be understood potentially larger hole groupings, both in terms of size and number, could be provided but probably with no additional benefits. Generally it is preferable that the holes are round and in a triangular distribution.

As indicated above, FIG. 3 illustrates a hole group 31 which comprises three holes 32 manufactured in a triangular pattern. Each hole 32 has a diameter d which is the same as its depth. Furthermore, within the hole group 31 each hole is spaced with a spacing s which is the same as the hole diameter d. In such circumstances, this spacing s is equal to the hole depth and the diameter d so that this value is denoted as a calibration value for the hole group. This calibration value is an integration of dimensions and possibly radiation absorption, as a reference of image quality.

Figure 4:
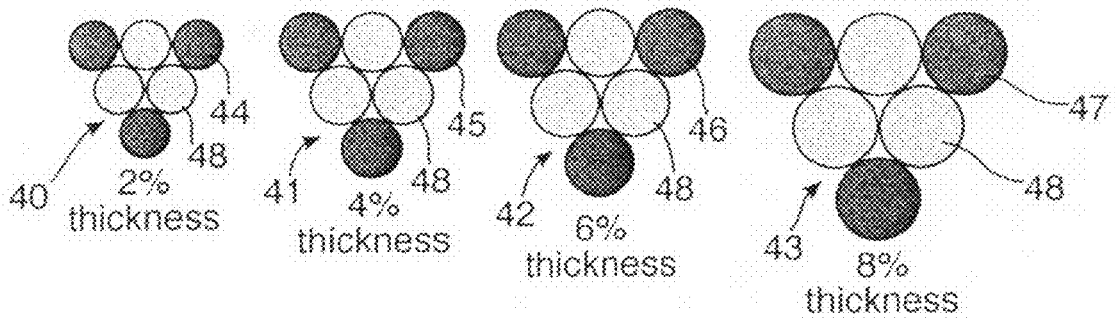
FIG. 4 is a schematic depiction illustrating a plurality of hole groups utilised in accordance with aspects of the present invention.

As will be described below, the uniformity with respect to spacing s, hole depth and diameter d provides an image quality indicator to be utilised as a reliability technique with respect to determining defects in an object. In order to achieve this, in this example, generally four hole groups are provided for each material thickness. The hole depth and diameters as well as spacings will typically be equivalent to 2 percent, 4 percent, 6 percent and 8 percent of the material thickness, as illustrated in FIG. 4. These values are typical and will provide a universal basis for image quality comparison and reference.

As can be seen in FIG. 4, as the calibration value is effectively defined by a percentage of material thickness, it will be understood that the hole groups generally increase in size. This is due to the hole diameter, hole spacing and hole depth being equivalent to that calibration value. FIG. 4 illustrates as indicated four hole groups 40, 41, 42, 43. As with FIG. 3, holes 44, 45, 46, 47 are arranged in a triangular pattern for each group 40, 41, 42, 43. For illustration purposes, shadow holes 48 are provided to indicate that the spacing between the respective holes 44, 45, 46, 47 in the groups 40, 41, 42, 43 are equivalent to the diameters of the holes.

For illustration purposes only, if a gauge has a material thickness of 2 mm it will be appreciated that for the 2 percent hole group 40 the calibration value will be 0.04 mm, for the 4 percent hole group 41 the calibration value will be 0.08 mm, for the 6 percent hole group 42 the calibration value will be 0.12 mm, whilst for the 8 percent hole group 43 the calibration value for the hole depth, diameter and spacing will be 0.24 mm. The calibration value is simply detected by multiplying the desired percentage by the thickness of the calibration gauge.

It will be understood that the calibration gauge as indicated may be a separate plate or formed integrally with a component to be inspected. In either event, the calibration values for the hole depth, diameter and hole spacing in a hole group will be the thickness of the plate or component at that part of the component to be inspected multiplied by the percentage ranged as indicated above.

In most instances, the image quality indicator is utilised in order to achieve a desired quality of inspection consistent with the requirements for the component. Thus, the level of inspection reliability required for low stress or components with low safety critical requirements may be less than that for highly stressed or high safety critical components. Thus, for example, the necessary level of contrast sensitivity and minimum level of spatial resolution will be determined for a component type. Unfortunately it has been found, particularly with regard to filmless inspection systems that merely specifying a particular contrast sensitivity does not simply correlate with a similar sensitivity with respect to detecting defect sizes. It will be understood that contrast sensitivity with respect to hole patterns as illustrated in FIGS. 3 and 4 in accordance with aspects of the present invention can be set by the lowest level of holes which can be readily distinguished by inspection visually of the image. Thus, if the 2 percent hole group 40 is clearly visible then it may be assumed that there is at least a 2 percent contrast sensitivity. This determination is more reliable in accordance with the calibration gauge in accordance with aspects of the present invention as the calibration gauge gives the minimum detectable defect size and integrates the contrast sensitivity and spatial resolution by the hole 44, 45, 46, 47 distributions and equivalence of the hole depth, diameter and spacings. By use of triangular patterns comprising three holes it will be understood that the interrogatory radiation detection system is tested with regard to its ability to differentiate between closely spaced volumetric defects. As indicated above, these volumetric defects comprise holes or cavities within the component where material is effectively removed or missing and therefore the attenuation and absorption of the interrogatory radiation varies across the component and this variation is then noted in the resultant image. If an inspector or radiographer or machine reader can see a clearly defined set of three holes, as indicated above, then this is an indication that the radiographic system is operating effectively at that level of sensitivity. However, if the holes are seen as blurred into one or are not visible at all then the radiographic system is not effective at that level of sensitivity and so defines a limitation upon the capability of that system or technique.

In terms of the method of using a calibration gauge in accordance with aspects of the present invention it will be appreciated that the gauge is either formed with an object to be inspected or a distinct element in the form of a plate or otherwise is created from a material the same as that from which the object is formed or a radiologically similar or quantifiably different material. Thus, when an interrogatory radiation, such as x-rays is presented to the calibration gauge a reference indication is provided as to the degree of resolution capability with regard to the inspection system utilising that interrogatory radiation. As indicated above, generally a plurality of hole groups will be provided with known graduation. These graduations may be 2%, 4%, 6%, 8% so that in the image provided by the inspection system as a result of the interrogatory radiation the highest levels of resolution will be provided by the last hole group which is clearly visible to a radiographer or other mechanism for inspecting the image. As indicated above, this resolution will relate to both spatial resolution as well as contrast sensitivity. In such circumstances it will be understood that the inspection system is thereby calibrated by the calibration gauge in accordance with aspects of the present invention in order to provide some reference as to the surety with respect to determining defects such as cracks within an object inspected by the inspection system using an interrogatory radiation such as x-rays.

As indicated above, radiographic systems depend upon penetration of the interrogatory radiation through the component to expose that component in forming an image. In such circumstances, with respect to defects, there is presented a cross-section which can typically be specified in terms of contrast sensitivity but due to the interrogatory radiation passing through the object there will be an attenuation and absorption dependent upon the thickness of the component under inspection. This attenuation and absorption is dependent upon the material from which the component under inspection is formed and so must be reflected in the calibration gauge both in terms of material type and thickness. It is this variation which provides the spatial resolution factor with regard to calibration. As indicated previously, separate calibration gauges for image quality indicators in respect of contrast sensitivity and spatial resolution have been provided in order to give generally an overview as to image quality but without a real indicator of the size of a defect that a system is capable of reliably detecting. By integrating in accordance with aspects of the present invention, the techniques used for contrast sensitivity as well as spatial resolution into one calibration gauge it will be understood a more quantifiable comparison is achieved based upon a minimal detectable defect size in the material type and thickness subject to inspection. The present calibration gauge provides an in situ reference for comparison.

As indicated, the calibration gauge may be a separable plate located adjacent to or upon the component to be inspected. If a separable component it will be appreciated that plates of different thickness and material type will be required for simulation to that of the component to be inspected. Alternatively, the hole groups may be drilled into a component to be inspected and then radiographic inspection performed. However, in such circumstances, integration of the calibration gauge into the component to be inspected must be carefully performed such that defects are not masked or defects effectively machined into the component at undesirable locations in terms of subsequent operational performance.

By aspects of the present invention as indicated, users of radiographic systems for component inspections will be able to determine for a particular component in terms of material type and thickness a minimum detectable defect size in subsequent inspections. As will be appreciated, the holes in the hole groups are incrementally differing in size. The increment in size will be chosen dependent upon a balance between a convenient number of hole groups and necessary accuracy. Thus, as indicated above, typically 2 percent, 4 percent, 6 percent and 8 percent of thickness will be used. By its nature, as indicated above, the hole groups will be inspected and the lowest hole group still clear will be determined as the minimum detectable defect size for the subject conditions in terms of material type and thickness. However, typically, the system will be able to operate at some point between that lowest defect size and the next level up in terms of sensitivity so, for example, if the 4 percent hole group is the last acceptable to the Inspector as being sufficiently clear, it will be appreciated in such circumstances that the 2 percent hole group is blurred or not visible at all but the system may still be sensitive at 3 percent but a hole group at that level has not been provided.

As indicated above, generally material thickness will be a particularly significant factor with regard to spatial resolution. In such circumstances, hole groups for each component thickness will be provided. This can be achieved by providing separate calibration gauges of each material thickness with appropriate holes in groups as described above or, alternatively, a gauge can be provided to assess material thicknesses over a range from a base level to an acceptable thickness. In the example given above, a gauge thickness in the order of 2 mm has been identified. In such circumstances, holes with a diameter dependent upon the percentage thickness increments as described will be provided for that 2 mm thickness. If the gauge is required to assess greater material thicknesses in accordance with aspects of the present invention a number of gauges of different thicknesses can be formed or 1 mm shims can be added to the base calibration base plate 50 to provide combinations of different thickness.

Figure 5:
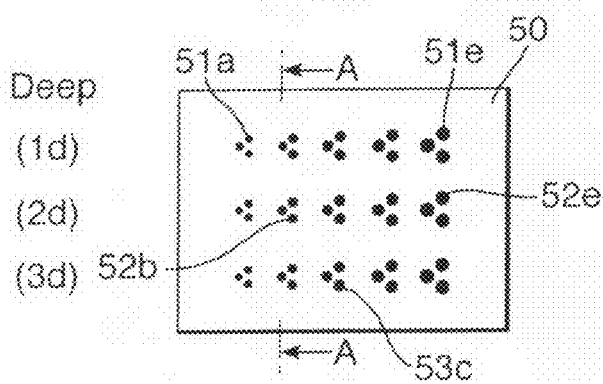
FIG. 5 is a schematic plan view of a calibration gauge in accordance with aspects of the present invention.
Figure 6:
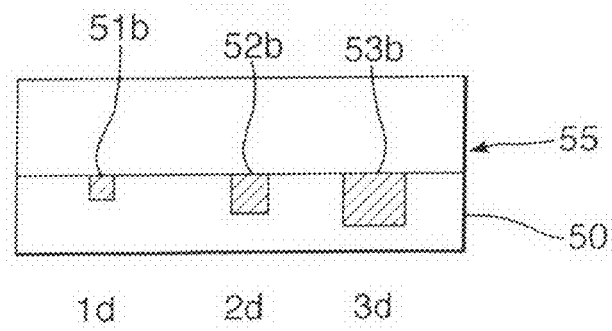
FIG. 6 is a schematic cross-section in the direction A-A of the plate depicted in FIG. 5.

FIG. 6 provides a schematic cross-section across A-A of FIG. 5. Thus, as can be seen, each hole group is provided with diameters 1*d*, 2*d*, 3*d* in the form of holes 51, 52, 53. These diameters 1*d*, 2*d*, 3*d*, as indicated above, will provide the calibration value for the diameter and depth of the holes 51, 52, 53 as well as the spacing within the triangular presentation between the holes 51, 52, 53. The diameters as indicated previously will be a percentage of the thickness of the plate 50. It will be understood that each hole group extends across the plate 50 and will have holes 51, 52, 53 with respective diameters but these diameters 1*d*, 2*d*, 3*d* will differ in each hole group. As illustrated there are five hole groups denoted (a), (b), (c), (d) and (e). Thus, by judicial choice of diameters 1*d*, 2*d*, 3*d* for each group (a), (b), (c), (d) and (e) it will be understood the calibration values for each gauge thickness defined by the base plate 50 thickness and those with shims 55 added.

In the above circumstances at a base sensitivity thickness level without a shim 55 associated with the plate 50 it will be understood a first hole group set (a) will be utilised. However, a shim 55 which may comprise a blank sheet of material of the same type as the plate 50 as well as the component to be inspected and having a thickness in incremental values consistent will be used with the other hole groups (b), (c), (d) and (e). In such circumstances, the diameters 1*d*, 2*d*, 3*d* will constitute appropriate percentage increments of the combined thickness of the shim 55 and the base plate 50 to reflect the thickness of the component to be inspected. In such circumstances, the base plate 50 will enable variation dependent upon the component thickness to be inspected to be achieved simply by adding shims 55 to the base plate 50. It will be appreciated that generally the shim 55 must be lapped or ground to a flat finish so ensure that there is a limited, if any, gap between the base plate 50 upper surface and the shim 55.

Variations and alterations to the above embodiments will be understood by those skilled in the art. Thus, for example, the percentage incremental size differentials between the hole groups and sets may be adjusted dependent upon requirements and particular material types.

The calibration value is generally a dimension defined as a percentage of the object or gauge thickness so that the same dimensions may be used for hole diameter, spacing and depth. However, where an accurate determination of the quotient for radiation absorption is known then some relative dimensional adjustment may be made in a distinct or separate gauge plate, particularly in terms of hole depth, by comparison of the radiation absorption quotients for the material of the object to be inspected and the material of the calibration gauge.

The invention claimed is:

1. A gauge for providing calibration when exposed to interrogatory radiation in an imaging system for inspecting an object, the gauge comprising:
   a material defining holes arranged in a plurality of hole groups, wherein
      the holes having a diameter, a depth and a spacing to other holes of the hole groups of substantially the same calibration value,
      the diameter provides a reference for assessing contrast resolution, whilst the depth and spacing of the holes provides a reference dependent upon attenuation of an interrogatory radiation in the material of the gauge between the holes for assessing spatial resolution, and
      each of the plurality of hole groups is integrally formed within the object for inspection.

2. A gauge as claimed in claim 1 wherein there are three holes in the hole group arranged in a triangular pattern.

3. A gauge as claimed in claim 1 wherein the calibration value is a percentage of a thickness of the gauge below each hole of the hole group.

4. A gauge as claimed in claim 1 wherein where there is a plurality of hole groups, the calibration values for respective groups are 2 percent, 4 percent, 6 percent and 8 percent of the thickness of the gauge.

5. A gauge as claimed in claim 1 wherein the gauge has a thickness in the order of 2 mm.

6. A gauge as claimed in claim 1 wherein the gauge has a variable thickness.

7. A gauge as claimed in claim 1 wherein the gauge is made from the same material as the object for inspection.

8. A gauge as claimed in claim 1 wherein the gauge is made from a material having substantially the same radiological nature as the material from which the object for inspection is formed.

9. A gauge as claimed in claim 1 wherein the interrogatory radiation is one of the group comprising X-rays, gamma radiation and neutron radiation.

* * * * *